United States Patent [19]
Juch

[11] Patent Number: 5,711,967
[45] Date of Patent: Jan. 27, 1998

[54] ORAL DICLOFENAC PREPARATION

[75] Inventor: Rolf-Dieter Juch, Wangen, Switzerland

[73] Assignee: Spirig AG, Pharmazeutische Praeparate, Switzerland

[21] Appl. No.: 231,458

[22] Filed: Apr. 21, 1994

Related U.S. Application Data

[63] Continuation of Ser. No. 899,500, Jun. 16, 1992, abandoned.

[30] Foreign Application Priority Data

Jun. 17, 1991 [EP] European Pat. Off. ......... 91810460.5

[51] Int. Cl.$^6$ ............... A61K 9/16; A61K 9/58; A61K 9/62
[52] U.S. Cl. ............... 424/462; 424/461; 424/494; 424/497
[58] Field of Search ............... 424/470, 473, 424/480, 482, 497, 494, 456, 461, 462; 427/214, 215

[56] References Cited

U.S. PATENT DOCUMENTS

| | | | |
|---|---|---|---|
| 4,871,549 | 10/1989 | Ueda et al. | 424/494 |
| 4,900,557 | 2/1990 | Dell et al. | 424/462 |
| 4,954,350 | 9/1990 | Jones et al. | 424/493 |
| 4,968,505 | 11/1990 | Okada et al. | 424/497 |
| 4,980,170 | 12/1990 | Schneider et al. | 424/462 |
| 5,026,560 | 6/1991 | Makino et al. | 424/497 |
| 5,068,112 | 11/1991 | Samejima et al. | 424/495 |
| 5,096,717 | 3/1992 | Wirth et al. | 424/494 |
| 5,102,668 | 4/1992 | Eichel et al. | 424/494 |

FOREIGN PATENT DOCUMENTS

| | | |
|---|---|---|
| 0383967 | 2/1989 | European Pat. Off. |
| 0421921 | 8/1990 | European Pat. Off. |
| 2635460 | 5/1989 | France |

*Primary Examiner*—Edward J. Webman
*Attorney, Agent, or Firm*—Lorusso & Loud

[57] ABSTRACT

The novel diclofenac preparation with controlled release is in the form of pellets. The active ingredient, applied to inert pellets, is coated with a membrane layer which contains, in addition to 35–65% by weight of a water-insoluble polymer, 5–20% by weight of at least one water-soluble and/or water-insoluble pore-forming agent and 20–50% by weight of adjuncts. The pore-forming agents permit a very uniform release of diclofenac such that administration twice a day is sufficient. A film coating resistant to gastric juice is applied over the membrane layer.

47 Claims, 3 Drawing Sheets

ORAL DICLOFENAC PREPARATION

This is a continuation of application Ser. No. 07/899,500 filed on Jun. 16, 1992 abandoned.

DEFINITIONS

Various trademarks appear throughout the disclosure to describe some of the chemical ingredients comprising the invention. They are identified as follows:

"MACROGOL" is a trademark of Hoechst AG, Frankfurt, Germany and identifies the product polyethylene glycol.

"SYLOID" is a trademark of Grace GmbH, Worms, Germany and identifies the product silicium dioxide.

"AEROSIL" is a trademark of Degussa AG, Frankfurt, Germany and identifies the product silicium dioxide.

"POVIDONE K 30" is a trademark of BASF, Ludwigshafen, Germany and identifies the product polyvinyl pyrrolidone.

"MACROGOL 400" is a trademark of Hoechst AG, Frankfurt, Germany and identifies the product polyethylene glycol 400.

"EUDRAGIT RL 30 D" is a trademark of Rohm Pharma Gmbh, Weiterstadt, Germany and identifies the product acrylic/methacrylic acid ester copolymerisates with one quaternary ammonium group in relation to 20 neutral (meth) acrylic acid ester groups.

"EUDRAGIT RS 30 D" is a trademark of Rohm Pharma Gmbh, Weiterstadt, Germany and identifies the product acrylic/methacrylic acid ester copolymerisates with one quaternary ammonium group in relation to 40 neutral (meth) acrylic acid ester groups.

"EUDRAGIT NE 30 D" is a trademark of Rohm Pharma Gmbh, Darmstadt, Germany and identifies the product copolymerisate with neutral character based on poly(meth)-acrylic acid esters.

"SURELEASE" or "SURELEASE XM" is a trademark of Colorcon, Orpington Kent, United Kingdom and identifies the product ethyl cellulose.

"POLYSORBAT 80" is a trademark of Atlas Chemie, Essen, Germany and identifies the product polyoxyethylene-20-sorbitan-monooleate.

"EUDRAGIT L" is a trademark of Rohm Pharma Gmbh, Weiterstadt, Germany and identifies the product methacrylic acid/ethyl acrylate copolymerisate with anionic character.

"EUDRAGIT S" is a trademark of Rohm Pharma Gmbh, Weiterstadt, Germany and identifies the product methacrylic acid/ethyl acrylate copolymerisate with anionic character.

"AQUATERIC" is a trademark of FMC, Philadelphia, Pa. and identifies the product cellulose acetate phthalate.

"DUODCEL" is a trademark of Lehmann & Voss, Hambourg, Germany and identifies the product carboxy methyl ethyl cellulose.

"EUDRAGIT L 30 D" is a trademark of Rohm Pharma Gmbh, Weiterstadt, Germany and identifies the product methacrylic acid copolymer type C.

The invention relates to a novel diclofenac preparation with controlled release of the active ingredient, as described in the claims.

For a long time, non-steroidal diclofenac has proved successful in the long-term therapy of rheumatic diseases on account of its potent antiinflammatory and analgesic action.

It is generally known, however, that the blood concentration half-life of oral diclofenac preparations is very short at one to two hours, which is why the drug normally has to be administered at least three times a day. However, the frequent administration of the drug is the cause of an unsatisfactory patient compliance; at the same time, reduced patient cooperation is also to be expected, especially because the patients are often of advanced age and have to take several different drugs every day, making it difficult to carry out a clinical check and to achieve the therapeutic result.

In addition, the side-effects caused by the rapid increase of active ingredient in the blood, e.g. a wide variety of gastrointestinal complaints, can be problematical. As the therapeutic treatment of a rheumatic inflammation always constitutes a compromise between a successful control of the symptoms, which requires an adequate blood plasma level of diclofenac, and an acceptance of undesirable side-effects, which, as is known, is decisively influenced by excessively high blood plasma values, attempts have already been made to control these side-effects by influencing the release of diclofenac.

Diclofenac is known to concentrate in the synovial fluid, with a delay, from the blood plasma. The blood plasma/synovial fluid exchange processes take place slowly in comparison with the plasma kinetics. It is therefore unnecessary to maintain a high blood plasma level over many hours. However, because the elimination half-life of non-delayed-action diclofenac is in the region of 1–2 hours, oral administration twice a day is not normally sufficient. Thus, in Tempo Medical (APV course on antirheumatics, Nürnberg 1983), Fenner mentions that even delayed-action forms of diclofenac are only of limited suitability for influencing the plasma level profile caused by the short blood plasma elimination half-lives so that a significant control of the blood plasma level can be effected even after 8 to 10 hours, because the delayed action leads after this period of time to a substantial flattening of the blood plasma level curve.

Therefore, in the development of novel pharmaceutical forms of administration, those skilled in the art are still faced with the problem on the one hand of maintaining the blood plasma level of diclofenac high enough for the action also to persist overnight, thereby avoiding symptoms like morning stiffness, for example, and on the other hand of getting diclofenac to start acting very soon after administration.

To achieve this aim it is frequently recommended to combine the administration of a coated tablet resistant to gastric juice with the administration of a suppository or delayed-action coated tablet before retiring. This can confuse the patient, with serious consequences, and lead to enhanced side-effects or deficient short-term analgesia.

To avoid this, attempts have been made to combine both active types of diclofenac in a single form of administration.

Japanese patent 61/44811 (publication date 4th Mar. 1986) claims a combination of an initial-release granule mixture with a delayed-release active ingredient component. As the active ingredient in the initial-release granule component is already released in the stomach, disadvantageous side-effects are to be expected because of the mucosa-irritating and/or mucosa-damaging action of diclofenac.

The granule component which releases diclofenac with a delay is coated with a shell containing methacrylic acid/methyl methacrylate copolymer, which dissolves in water at a pH of 6–7. This shell tends to break during coating and drying. The fragments display a tendency to agglomerate. On the one hand this reduces the yield of particles of the desired size, and on the other hand it compromises the delayed-release action of these particles.

Another step in the development of diclofenac formulations consists in mitigating the above disadvantages. Thus European patent 348 808 describes a pelleted oral diclofenac preparation in which the active ingredient is partly in a delayed-release form and partly in a form resistant to gastric juice. This aim is achieved by coating some of the pellets with a diffusion membrane of delayed permeability to diclofenac, and some pellets with a membrane resistant to gastric juice. The diffusion membrane here consists of at least one layer of an acrylic resin. As diclofenac has an acid character with a pKa of approx. 4–5, its primary solubility in aqueous media increases considerably above this value. There is also generally a concomitant increase in the interaction with the polymers used to provide pellets with a shell resistant to gastric juice. If diclofenac is administered at the same time as food is eaten, the consequential increase in the pH to approx. 5 in the stomach can then cause the active ingredient to be completely released prematurely. A suggested way of preventing this is to have a two-layer membrane resistant to gastric juice, consisting of cellulose ether with a variable degree of substitution, which is esterified with phthalic anhydride, a water-insoluble organic acid being incorporated in its inner layer as an adjunct.

The aim of the invention described in European patent 383 967 is to provide a pelleted oral diclofenac preparation with a prolonged action and an improved shell resistant to gastric juice, so that the particles no longer agglomerate.

The problem is solved by a preparation consisting partly of quick-release diclofenac and partly of pellets with a shell resistant to gastric juice. The shell is made up of 100 parts of methacrylic acid/methyl methacrylate copolymer, 3–40 parts of glycerol fatty acid ester and 1–150 parts of talc.

German Offenlegungsschrift 39 15 150 also claims a long-acting diclofenac preparation comprising one component with rapid release of the active ingredient and one component with delayed release of the active ingredient. Here the component containing diclofenac with delayed release is mixed with an organic acid and the mixture is provided with a conventional shell.

In the above-mentioned combination preparations, one quick-release and one delayed-release diclofenac are mixed together and then generally pressed to form tablets or filled into capsules. It is complicated, however, to prepare a quantitatively exact mixture. Filling two components into a capsule from a mixture is problematical because of possible inhomogeneities; filling two components separately is technically more expensive and is not advisable for such small filling quantities because of the required dosage accuracy.

As even small variations in the quantitative composition or inhomogeneous mixing of the components of a diclofenac preparation can give rise to significant variations in the blood plasma value, it would be of great advantage to provide a diclofenac preparation, with controlled release of the active ingredient, which consisted of only one component.

One object of the present invention is therefore to provide an oral preparation containing diclofenac, with controlled release of the active ingredient, whose administration is followed as quickly as possible by analgesia which is maintained over a prolonged period of time of approx. 12 hours. In the present specification, diclofenac means the free acid and its salts, especially diclofenac Na.

Other objects of the invention consist in achieving a maximum degree of reproducibility for the release of the active ingredient, not using organic solvents when building up the preparation, so as to avoid solvent residues in the end product, and ensuring that the release characteristic remains stable over several years when the preparation is stored under normal conditions.

These objects have been achieved according to the invention by a pelleted oral drug preparation containing diclofenac, with controlled release of the active ingredient, which contains an active ingredient layer applied to an inert pellet, an inner membrane layer preferably making up 10–20% by weight of the final pellets, 35–65% by weight, preferably 45–55% by weight, of the membrane layer consisting of at least one water-insoluble polymer, 5–20% by weight, preferably 6–13% by weight, consisting of at least one pore-forming agent and up to 20–50% by weight, preferably 25–46% by weight, consisting of adjuncts, and an outer film coating resistant to gastric juice.

Preferably, the drug preparation according to the invention in pellet form is enclosed in a capsule, particularly preferably in a hard gelatin capsule.

The existing problems with the manufacture and administration of diclofenac preparations are extensively solved by the multiple-unit drug form according to the invention.

The active ingredient layer contains the active ingredient and adjuncts, which according to the invention are applied to commercially available inert pellets (placebos).

Suitable grain sizes of the inert pellets have a diameter of 0.5 mm to 1.2 mm, preferably 0.6 mm to 0.85 mm, with less than 5% by weight of oversizes and/or undersizes. The build-up with diclofenac is then carried out by conventional application techniques, e.g. in rotating kettles, but preferably in fluidized-bed spray units, which are preferably equipped with a Wurster insert or rotor processor insert.

Diclofenac is preferably added as a suspension in water which preferably contains, as adjuncts, binders such as povidone or cellulose derivatives, e.g. hydroxypropyl cellulose or hydroxypropyl methyl cellulose, plasticizers such as macrogol, and lubricants and/or release agents such as talc, magnesium stearate, Syloid or Aerosil, and if necessary a silicone antifoam emulsion. Nicotinamide, for example, can be added to the suspension as an "indicator" for checking the resistance to gastric juice, according to Swiss patent 656 310.

As particularly preferred adjuncts, a mixture is used which contains povidone K 30, macrogol 400 and talc or magnesium stearate, and if necessary a silicone antifoam, and/or nicotinamide as an indicator.

The suspension containing diclofenac is preferably applied to the inert pellets by spraying. The inert pellets loaded in this way with the active ingredient layer are dried to a residual moisture content of 0.1–4.0% by weight, preferably 0.4–1.0% by weight, based in each case on the uncoated pellets. The build-up of the active ingredient layer is complete when the weight of the inert pellets has increased by 110–160% by weight, preferably 130–140% by weight. Preferably, this method is used to prepare pellets containing 20–45% by weight of active ingredient and 1–15% by weight of adjuncts, based on the final pellets (the final pellets being the pellets coated twice according to the invention).

The pellet size suitable for the reproducibility of the release, in the range from 0.6 mm to 1.4 mm, preferably 0.8 mm to 1.25 mm, can be sorted out by sieving the pellets.

The desired release of the active ingredient is determined especially by the build-up of the inner membrane layer and the outer film coating.

The inner membrane layer controls the diffusion of diclofenac from the inside of the pellet into the surrounding fluid. To control the diffusion characteristic and to assure the desired release of diclofenac, it is necessary that this layer should not disintegrate or dissolve during the diffusion and the loss of active ingredient from the pellet, but should only shrink; it should nevertheless release the active ingredient in the desired amount. One inner diffusion membrane layer is absent water-soluble cellulose derivatives.

This aim is achieved by the application of a mixture containing at least one suitable water-insoluble polymer such as water-insoluble acrylic resins, e.g. acrylic acid/methacrylic acid ester copolymers like those marketed under the name Eudragit RL 30 D, Eudragit RS 30 D or Eudragit NE 30 D by Röhm, Darmstadt, Germany, Surelease or Surelease XM in an amount of 35–65% by weight, preferably 45–55% by weight, at least one suitable water-soluble or water-insoluble pore-forming agent, or a mixture thereof, in an amount of 5–20% by weight, preferably 6–13% by weight, and adjuncts such as plasticizers like triacetin or diethyl phthalate, or lubricants like talc, magnesium stearate, Syloid or Aerosil, and if necessary antifoam emulsions, preferably a silicone antifoam emulsion, in an amount of 20–50% by weight, preferably 25–45% by weight, based in each case on the membrane layer.

Examples of water-insoluble pore-forming agents which can be used are kaolin, calcium carbonate, calcium hydrogen phosphate, magnesium oxide, microcrystalline cellulose, titanium dioxide or iron oxide.

Examples of water-soluble pore-forming agents which can be used are povidone K 30, polyvinyl alcohol, cellulose derivatives such as hydroxypropyl cellulose, hydroxypropyl methyl cellulose, methyl cellulose or sodium carboxymethyl cellulose, sucrose, xylitol, sorbitol, mannitol, maltose, xylose, glucose, potassium chloride, sodium chloride, polysorbate 80, polyethylene glycol, propylene glycol or sodium citrate.

A single pore-forming agent can be used here, but it is also possible to use a mixture of water-insoluble or water-soluble pore-forming agents or a mixture of water-soluble and water-insoluble pore-forming agents.

It is preferable to use a mixture of pore-forming agents comprising povidone K 30, polysorbate 80 and red iron oxide.

The membrane layer can be applied in various ways known per se. Favorable results are obtained especially by spraying an aqueous suspension of the agents forming the membrane layer on to the preformed pellets, preferably in a fluidized-bed spray unit. It is particularly preferable for the fluidized-bed spray unit to contain a Wurster insert or a rotor processor insert.

The weight of the membrane layer is preferably 10–20% of the final pellets. The proportion is preferably about 15±2% by weight, a change in the amount having a substantial influence on the release characteristic.

Preferred embodiments of the membrane layer applied contain e.g. the following, in % by weight of the membrane layer:

| | |
|---|---|
| Eudragit NE 30 D | 45% to 55%, pref. 52.0–53.5% |
| Povidone K 30 | 5% to 10%, pref. 8.8–9.8% |
| Polysorbate 80 | 0.5% to 1.5%, pref. 1.3% |
| Red iron oxide | 0.5% to 1.5%, pref. 0.8–1.0% |
| Talc | 15% to 30%, pref. 22.0–22.8% |
| Magnesium stearate | 10% to 15%, pref. 13.0–13.4% |
| Antifoam emulsion SE2 | 0.01% to 0.1%, pref. 0.05% |

Eudragit NE 30 D is used here as a layer-forming water-insoluble copolymer. The task of the pore-forming agents is to dissolve or break out of the membrane layer in the intestinal tract, so that the surrounding fluid can diffuse into the pellet and dissolve the diclofenac present therein. The dissolved diclofenac can then be released through the pores of the membrane layer into the gastrointestinal tract in accordance with the intended release characteristic. By virtue of the predefined build-up of the membrane layer, practically all the active ingredient present is absorbed by the body.

A further advantage of the membrane layer according to the invention is that a dosage interval of 12 hours for the preparation is sufficient without giving rise to the harmful accumulation of active ingredient in the blood plasma, even though a relatively high initial concentration can be attained, thereby promoting an early transfer of the active ingredient into the synovial fluid.

A further process involves the application of a film coating resistant to gastric juice, which dissolves above a pH of 5.5. This coating, which preferably makes up 5–20% by weight of the final pellets, and particularly preferably 10–16% by weight, is preferably sprayed on. The actual film coating resistant to gastric juice contains preferably 60–90%, particularly preferably 75% by weight, of at least one acid-insoluble polymer and 10–40%, particularly preferably 25% by weight, of adjuncts.

Examples of possible acid-insoluble polymers are methacrylic acid/methacrylic acid ester copolymers or methacrylic acid/acrylic acid ester copolymers such as Eudragit L, Eudragit S, Eudragit RL 30 D and/or Eudragit RS 30 D, or Aquateric or Duodcel, preferably Eudragit L 30 D.

Possible adjuncts are plasticizers such as diethyl phthalate, triacetin, dibutyl sebacate, diethyl adipate, polyethylene glycol or tributyl citrate, and lubricants and/or release agents such as talc or Syloid, or colored pigments such as iron oxide or titanium dioxide, and if necessary a silicone antifoam emulsion such as that sold e.g. under the name SE 2 by Wacker.

A preferred form of the film coating resistant to gastric juice contains 70–80% by weight of Eudragit L 30 D, 10–20% by weight of diethyl phthalate, 5–15% by weight of talc and if necessary 0.1–0.5% by weight (solids content 0.02–0.1% by weight) of a silicone antifoam, based in each case on the film coating.

The film coating resistant to gastric juice is preferably applied up to a proportion of 5–20% by weight of the final pellets, particularly preferably approx. 10–16% by weight. If the coating does not satisfy the criteria for resistance to gastric juice as laid down in USP XXII, p. 1580, the thickness of the film coating can be increased by additional application. The aqueous suspension according to the invention for applying the film coating resistant to gastric juice has an excellent processability, it being possible for the application per se to be carried out in a conventional manner. Preferably, however, the agents forming the film coating resistant to gastric juice are sprayed on as an aqueous suspension in a fluidized-bed spray unit with a Wurster insert or rotor processor insert.

The pellets coated with the film coating resistant to gastric juice are sieved and graded in order to remove agglomerates and any fragments present. The fraction between 0.6 mm and 1.4 mm, preferably of 0.8 mm to 1.25 mm, is outstandingly suitable for the release of diclofenac with the following in vitro parameters (USP XXII, p. 1580):

>15% after 1 hour
>30% after 2 hours
>50% after 3 hours
>70% after 4 hours
>80% after 5 hours.

Figure 1:
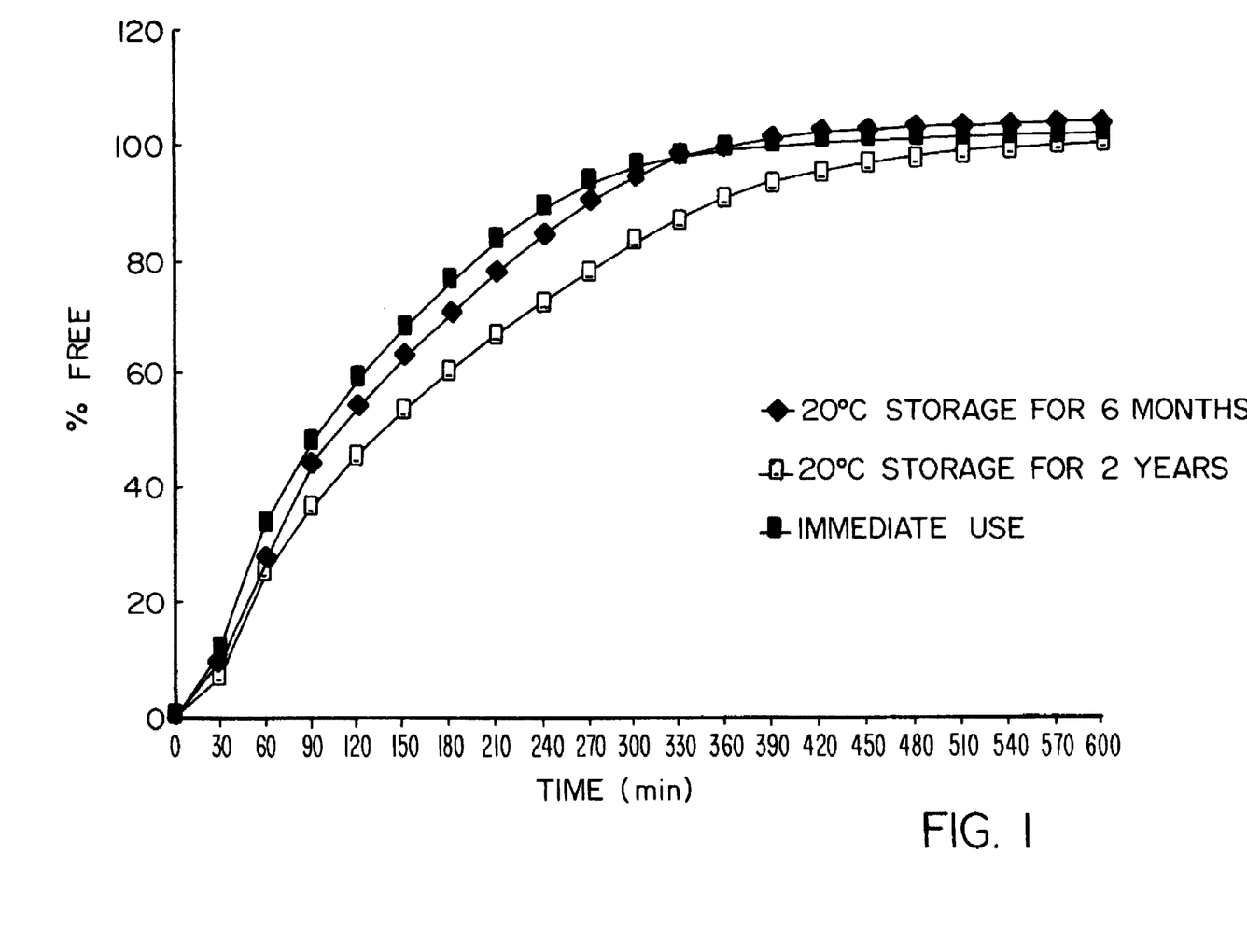
FIG. 1 shows in vitro release kinematics after six months storage, two years storage and without previous storage.

The film coating according to the invention has a good long-term stability such that the release kinematics in vitro remain substantially unchanged even after storage for 2 years (cf. FIG. 1).

Because on the one hand the individual pellet layers can themselves be built up in variable proportions within certain limits, and on the other hand the relative proportions of the individual layers used to build up the final pellets can also vary, the percentages have been based in some cases on the individual layers and in others on the final pellets.

The composition of preferred final pellets will now be given below according to type and according to proportions in % by weight:

| a) Inert pellet | 20% to 45%, pref. 31.0–33.3% |
|---|---|
| b) Active ingredient layer[+)]: | |
| Diclofenac Na | 20% to 45%, pref. 31.0–33.3% |
| Adjuncts | 1% to 15%, pref. *) |
| c) Membrane layer[+)]: | |
| Eudragit NE 30 D (solids content) | 6% to 14%, pref. 7.0–8.0% |
| Povidone K 30 | 0.5% to 4%, pref. 1.2–1.5% |
| Polysorbate 80 | 0.05% to 1%, pref. 0.17–0.2% |
| Red iron oxide | 0.05% to 3%, pref. 0.11–0.15% |
| Adjuncts preferably Talc | 1% to 6%, pref. 2.9–3.5% |
| Magnesium stearate | 0.5% to 3%, pref. 1.75–2.0% |
| +) containing a silicone antifoam emulsion | |
| *) povidone K 30 | 3.3–6% |
| macrogol 400 | 0.5–1% |
| talc | 2% |
| if necessary nicotinamide or (instead of talc and if appropriate nicotinamide) magnesium stearate | 3% 0.2% |
| d) Film coating[+)]: | |
| Eudragit L 30 D (solids content) | 5% to 15%, pref. 7.5–11.9% |
| Diethyl phthalate Talc | 1% to 8%, pref. **) |

Two particularly preferred formulations contain:
a) Inert pellet 31.0%
b) Active ingredient layer[+)]: diclofenac Na 31.0%, povidone K 30 6%, macrogol 400 1%, talc 2%, nicotinamide 3%
c) Membrane layer[+)]: Eudragit NE 30 D 6 8.0% (solids content), povidone K 30 1.5%, polysorbate 80 0.2%, red iron oxide 0.15%, talc 3.5%, magnesium stearate 2.0%
d) Film coating[+)]: Eudragit L 30 D 7.5% (solids content), diethyl phthalate 1.5%, talc 1%; and a) Inert pellet 33.3%
b) Active ingredient layer[+)]: diclofenac Na 33.3%, povidone K 30 3.3%, macrogol 400 0.5%, magnesium stearate 0.2%
c) Membrane layer[+)]: Eudragit NE 30 D 6 7.0% (solids content), povidone K 30 1.2%, polysorbate 80 0.17%, red iron oxide 0.11%, talc 2.9%, magnesium stearate 1.75%
d) Film coating[+)]: Eudragit L 30 D 11.9% (solids content), diethyl phthalate 2.4%, talc 1.6%.

+) containing a silicone antifoam emulsion

The pellets are preferably filled into capsules, particularly preferably into hard gelatin capsules. The therapeutic requirement is a filling quantity of 50 mg to 150 mg of diclofenac per capsule, preferably 75 mg (corresponding to approx. 155 mg to 465 mg of pellets).

| **) diethyl phthalate | 1.5–2.4% |
|---|---|
| talc | 1–1.6% |

With the preferred dose of diclofenac, and with the release characteristic which is to be standardized and can be checked under in vitro conditions, the active ingredient is almost completely absorbed by the body. The maximum blood plasma values are in the region of 300 ng/ml and the active ingredient plateau is maintained in the serum for several hours because of the delayed release of the active ingredient.

Even when a capsule according to the invention containing e.g. 75 mg of diclofenac is administered every 12 hours over a prolonged period, no increase in the blood plasma values can be observed because the maximum concentrations are always reached within a very short period of time.

Figure 2:
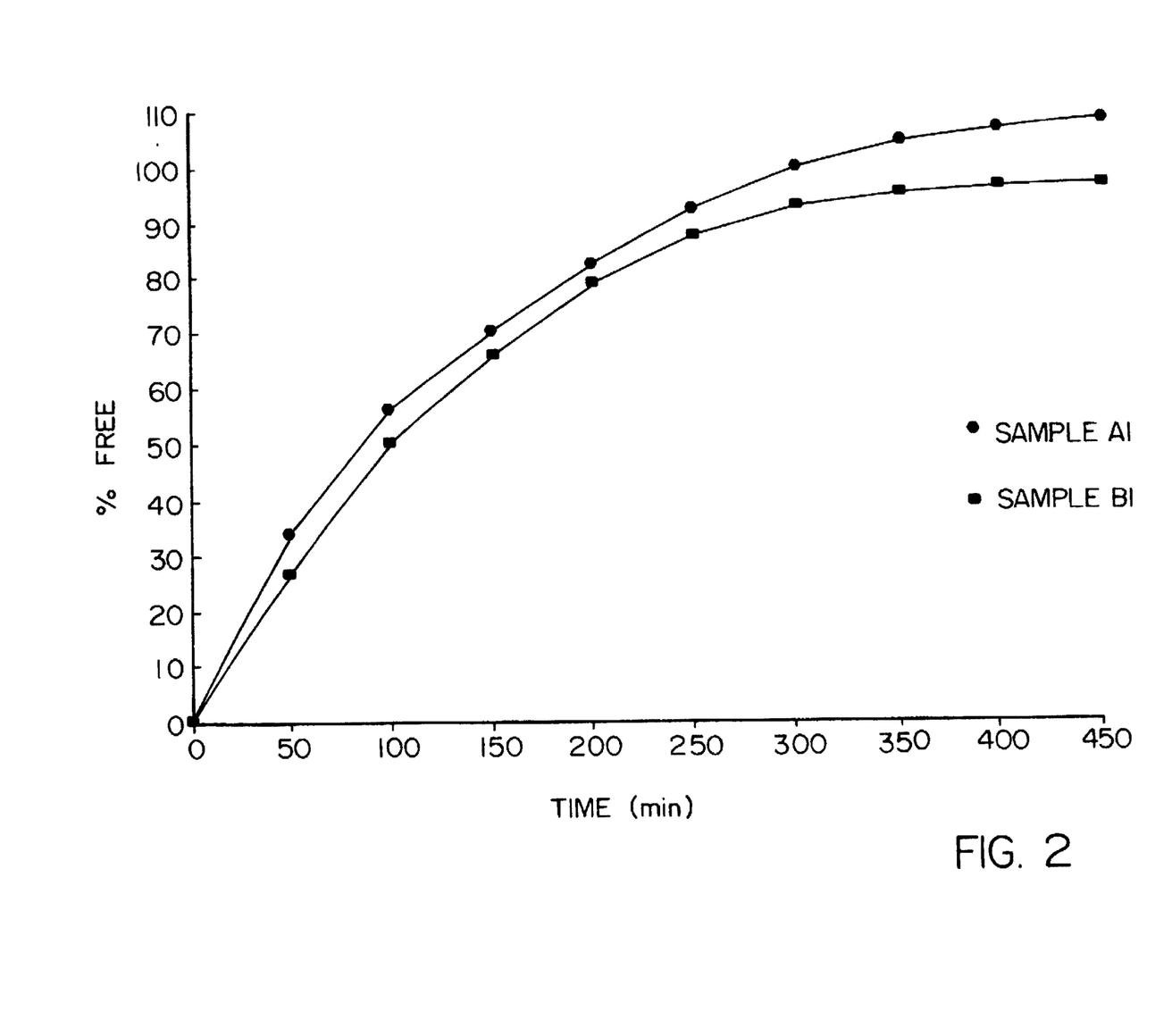
FIG. 2 shows in vitro release kinematics of two samples A1 and B1 of a diclofenac preparation in intestinal juice after two hours pretreatment with gastric juice.
Figure 3:
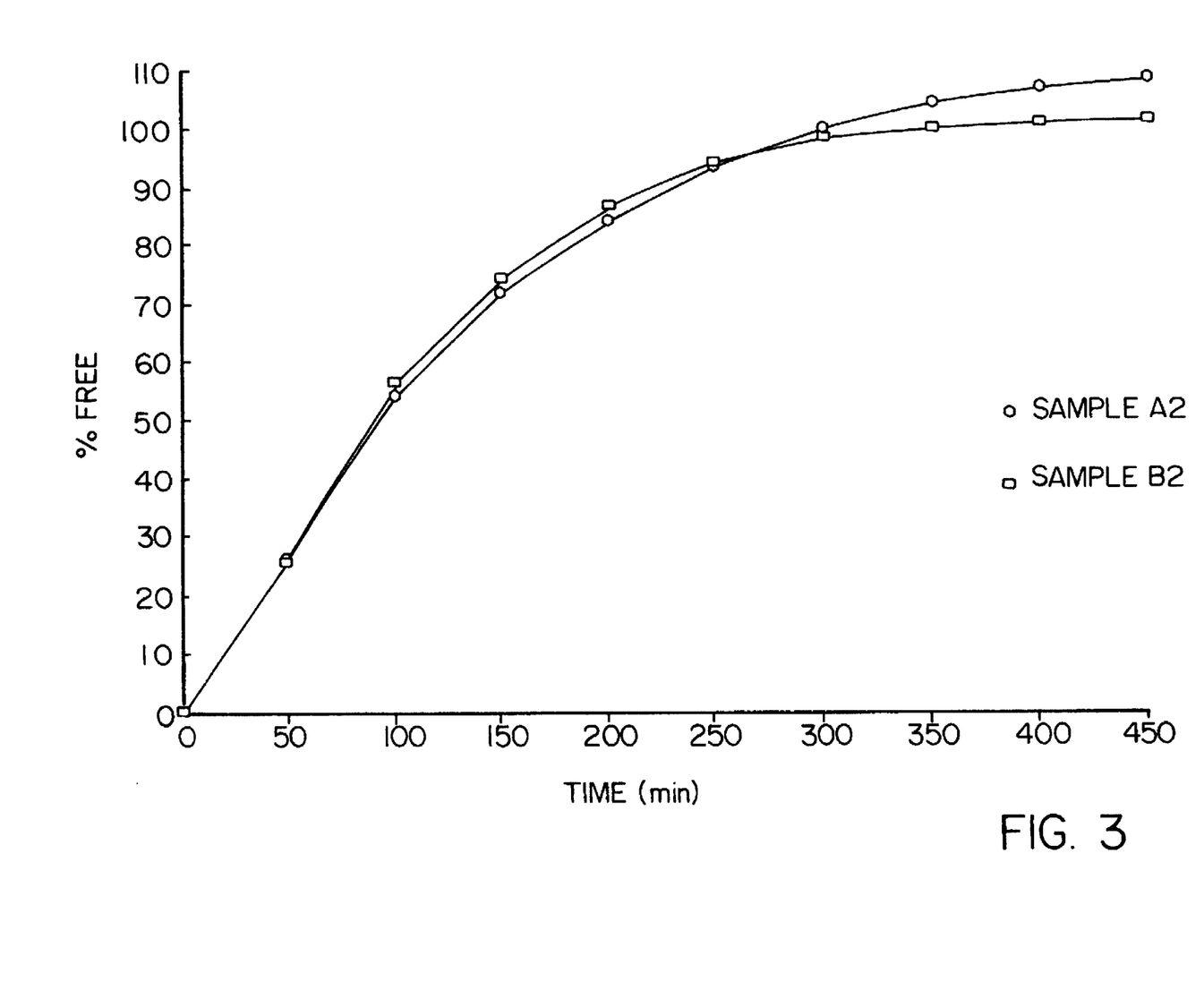
FIG. 3 shows in vitro release kinematics of two samples A2 and B2 without pretreatment with gastric juice.

A further advantage of the invention is that—in contrast to the state of the art—the release of diclofenac does not depend on whether the preparation has been subjected to a two-hour in vitro pretreatment with gastric juice. This is shown in FIG. 2 and FIG. 3, where the mean values of the release in synthetic intestinal juice from 2 different production batches of a diclofenac preparation according to the invention containing 75 mg were measured in one case (FIG. 2, sample A1 and sample B1) with and in one case (FIG. 3, sample A2 and sample B2) without a two-hour pretreatment with gastric juice.

This in vitro experiment was based on the US paddle method and carried out with a SOTAX AT6 apparatus according to USP XXI. The mean dissolution time (which represents the time interval up to the release of 63.2% of active ingredient) was approx. 2 hours and independent of the pretreatment.

The mean residence time (MRT) of the active ingredient is approx. 5.5 hours in a preferred embodiment.

The small standard deviations and the lack of influence of a two-hour pretreatment with gastric juice are proof of the uniform behavior of the release of diclofenac from a drug preparation according to the invention under very diverse conditions. This leads in vivo to a reduced dispersion of the blood plasma concentrations and is of prime importance for the blood plasma concentration profiles of diclofenac, which are known to be inherently very susceptible to variation.

One particular advantage of the preparation according to the invention is therefore that the results which can be obtained by the daily administration of a 2×75 mg preparation according to the invention are comparable to those of a 3×50 mg standard dose and better than those of 2×100 mg delayed-action doses according to the state of the art.

The preparation of the coated pellets can be carried out by conventional methods, but it is preferable to use the fluidized-bed spray method. If this method is applied and the described adjuvants are used, it is not necessary to use any organic solvents, so no solvent residues can be present in the end product. In addition, the uncomplicated and economic method of preparation makes it possible to achieve a maximum degree of reproducibility of the release, and the uniform build-up of the pellets makes it possible to assure a reliable dosage when filling into capsules.

The invention is illustrated in greater detail below with the aid of Examples:

EXAMPLE 1

Formula for the preparation of 256 kg of pellets

| Inert pellets | 80 kg |
|---|---|
| Active ingredient layer (suspension A) | |
| Aqua purificata | 240 kg |
| Silicone antifoam emulsion with a solids content of 0.13 kg | 0.65 kg |
| Diclofenac sodium | 80 kg |
| Nicotinamide | 8 kg |
| Povidone 30 | 16 kg |
| Macrogol 400 | 2.4 kg |
| Talc | 4.8 kg |

| Membrane layer (suspension B) | |
|---|---|
| Aqua purificata | 53 kg |
| Eudragit NE 30 D with a solids content of 21 kg | 70 kg |
| Polysorbate 80 | 0.5 kg |
| Povidone with a K value of 30 | 3.5 kg |
| Red iron oxide E 172 (CI 77491) | 0.35 kg |
| Talc | 9 kg |
| Magnesium stearate | 5 kg |
| Silicone antifoam emulsion with a solids content of 0.02 kg | 0.1 kg |

| Film coating (suspension C) | |
|---|---|
| Aqua purificata | 53 kg |
| Eudragit L 30 D with a solids content of 19.2 kg | 64 kg |
| Diethyl phthalate | 3.8 kg |
| Talc | 2.7 kg |
| Silicone antifoam emulsion with a solids content of 0.02 kg | 0.1 kg |

The inert pellets are placed in a fluidized-bed spray unit equipped with a Wurster insert and are sprayed with suspension A. The conditions depend on the type of apparatus and the progress of the spraying process.

Following the application of the active ingredient layer in a fluidized-bed spray unit equipped with a Wurster insert, the pellets are sprayed with suspension B and with suspension C.

The exit air temperature is max. 50° C. in the case of suspension A and max. 40° C. in the case of suspensions B and C. The relative humidity (hygro-control aw2 from Stankowitz, Diepholz, Germany) is 25 to 40% by weight. Sieving and grading are carried out using 0.8 mm and 1.4 mm netting sieves. The grain size distribution (sieve analysis) is typically in the range <0.2% by weight of <0.8 mm and <0.2% by weight of >1.4 mm. The yield is 90–98% by weight.

EXAMPLE 2

Formula for the preparation of 199.5 kg of pellets

| Inert pellets | 66.6 kg |
|---|---|
| Active ingredient layer (suspension A) | |
| Aqua purificata | 190 kg |
| Silicon antifoam emulsion with a solids content of 0.13 kg | 0.65 kg |
| Diclofenac sodium | 66.6 kg |
| Povidone 30 | 6.6 kg |
| Macrogol 400 | 1.0 kg |
| Magnesium stearate | 0.4 kg |

| Membrane layer (suspension B) | |
|---|---|
| Aqua purificata | 25 kg |
| Eudragit NE 30 D with a solids content of 14 kg | 47 kg |
| Polysorbate 80 | 0.34 kg |
| Povidone with a K value of 30 | 2.4 kg |
| Red iron oxide E 172 (CI 77491) | 0.22 kg |
| Talc | 5.8 kg |
| Magnesium stearate | 3.5 kg |
| Silicone antifoam emulsion with a solids content of 0.02 kg | 0.1 kg |

| Film coating (suspension C) | |
|---|---|
| Aqua purificata | 25 kg |
| Eudragit L 30 D with a solids content of 23.8 kg | 79 kg |
| Diethyl phthalate | 4.8 kg |
| Talc | 3.2 kg |
| Silicone antifoam emulsion with a solids content of 0.02 kg | 0.1 kg |

The method of preparation is carried out analogously to Example 1.

EXAMPLE 3

Formula for the preparation of 205 kg of pellets

| Inert pellets | 80 kg |
|---|---|
| Active ingredient layer (suspension A) | |
| Aqua purificata | 209 kg |
| Diclofenac sodium | 80 kg |
| Hydroxypropyl methyl cellulose | 8 kg |
| Syloid 244 FP | 2 kg |
| Silicone antifoam emulsion with a solids content of 0.1 kg | 0.5 kg |

| Membrane layer (suspension B) | |
|---|---|
| Aqua purificata | 30 kg |
| Eudragit NE 30 D with a solids content of 9.0 kg | 30 kg |
| Talc | 8 kg |
| Silicone antifoam emulsion with a solids content of 0.02 kg | 0.1 kg |

| Film coating (suspension C) | |
| --- | --- |
| Aqua purificata | 26 kg |
| Eudragit L 30 D with a solids content of 12 kg | 40 kg |
| Dibutyl sebacate | 2.5 kg |
| Talc | 3.5 kg |
| Silicone antifoam emulsion with a solids content of 0.02 kg | 0.1 kg |

The method of preparation is carried out analogously to Example 1.

EXAMPLE 4

| Formula for the preparation of 219 kg of pellets | |
| --- | --- |
| Inert pellets | 80 kg |
| Active ingredient layer (suspension A) | |
| Aqua purificata | 230 kg |
| Diclofenac sodium | 80 kg |
| Hydroxypropyl cellulose | 10 kg |
| Magnesium stearate | 1 kg |
| Nicotinamide | 8 kg |
| Silicone antifoam emulsion with a solids content of 0.02 kg | 0.1 kg |

| Membrane layer (suspension B) | |
| --- | --- |
| Aqua purificata | 26 kg |
| Eudragit RL 30 D with a solids content of 3.0 kg | 10 kg |
| Eudragit RS 30 D with a solids content of 9.0 kg | 30 kg |
| Triacetin | 2.5 kg |
| Talc | 3.5 kg |
| Silicone antifoam emulsion with a solids content of 0.01 kg | 0.05 kg |

| Film coating (suspension C) | |
| --- | --- |
| Aqua purificata | 78 kg |
| Aquateric | 15 kg |
| Diethyl phthalate | 5 kg |
| Polysorbate 80 | 0.2 kg |
| Titanium dioxide | 2 kg |

The method of preparation is carried out analogously to Example 1.

EXAMPLE 5

Formula for the preparation of 134 kg of pellets

| Inert pellets | 40.0 kg |
| --- | --- |
| Active ingredient layer (suspension A) | |
| Aqua purificata | 90.0 kg |
| Diclofenac sodium | 40.0 kg |
| Nicotinamide | 4.0 kg |
| Povidone K 30 | 1.0 kg |
| Talc | 2.0 kg |
| Silicone antifoam emulsion with a solids content of 0.06 kg | 0.3 kg |

| Membrane layer (suspension B) | |
| --- | --- |
| Aqua purificata | 38.0 kg |
| Eudragit NE 30 D with a solids content of 15.3 kg | 51.0 kg |
| Red iron oxide | 0.25 kg |
| Polysorbate 80 | 0.35 kg |
| Talc | 6.5 kg |
| Magnesium stearate | 3.5 kg |
| Hydroxypropyl methyl cellulose | 2.5 kg |
| Silicone antifoam emulsion with a solids content of 0.02 kg | 0.1 kg |

| Film coating (suspension C) | |
| --- | --- |
| Aqua purificata | 38.0 kg |
| Eudragit L 30 D with a solids content of 13.8 kg | 46.0 kg |
| Diethyl phthalate | 2.8 kg |
| Talc | 2.0 kg |
| Silicone antifoam emulsion with a solids content of 0.02 kg | 0.1 kg |

The method of preparation is carried out analogously to Example 1 with the following exceptions:

The inert pellets are placed in a fluidized-bed spray unit equipped with a rotor processor insert and are sprayed with suspension A for 5 min at a rate of 200 g/min. The inner cylinder is then opened to a slit height of 10 mm. The process air is adjusted to 1000 to 1500 m³/h. As the spraying process progresses, the spraying rate can be raised continuously up to 400–500 g/min.

Following the application of the active ingredient layer in a rotor processor, the pellets are sprayed with suspensions B and C.

The exit air temperature is 30–40° C. for all 3 spraying suspensions. The disk rotates at 500–900 rpm.

What is claimed is:

1. A pelleted oral drug preparation comprising:
   an active ingredient layer including an active ingredient consisting of diclofenac or one of its salts, with controlled release of the active ingredient, the active ingredient layer surrounding an inert pellet;
   an inner diffusion membrane layer absent water-soluble cellulose derivatives containing
   (i) 35–65% by weight of a pH independent water-insoluble polymer,
   (ii) 5–20% by weight of at least one pore-forming agent, and
   (iii) 20–50% by weight of adjuncts,
   wherein said inner diffusion membrane layer surrounds said active ingredient layer and further wherein said inner diffusion membrane layer is built to determine the release of said active ingredient; and
   an outer film coating resistant to gastric juice, the film coating surrounding said inner diffusion membrane layer and comprising 5–20% by weight based on the final pellet, wherein said film coating is soluble above a pH of 5.5, said film coating further comprising at least one acid insoluble polymer and adjuncts, the at least one acid insoluble polymer selected from the group consisting of methacrylic acid/methacrylic acid ester copolymers, methacrylic acid/acrylic acid ester copolymers, carboxy methyl ethyl cellulose, cellulose acetate phthalate, and mixtures thereof.

2. A drug preparation according to claim 1 wherein the inner membrane layer makes up 10–20% by weight of the final pellets.

3. A drug preparation according to claim 1 or wherein the active ingredient layer contains 20–45% by weight of active ingredient and 1–15% by weight of adjuncts, based on the final pellets.

4. A drug preparation according to claim 1 wherein the adjuncts comprising the active ingredient layer include at least one binder.

5. A drug preparation according to claim 1 wherein the inner membrane layer contains acrylic acid and methacrylic acid ester copolymerisates with one quaternary ammonium group in relation to 20 neutral acrylic and methacrylic acid ester groups; acrylic and methacrylic acid ester copolymerisates with one quaternary ammonium group in relation to 40 neutral acrylic and methacrylic acid ester groups; copolymerisate with neutral character based on polyacrylic and methacrylic acid esters; and/or ethyl cellulose, as the water-insoluble polymer.

6. A drug preparation according to claim 1 wherein the membrane layer contains water-insoluble agents, or water-soluble agents, or a mixture of water-soluble and water-insoluble agents as pore-forming agents, said water-insoluble agents and said water-soluble agents not being elemental metals.

7. A drug preparation according to claim 6 wherein kaolin, calcium carbonate, calcium hydrogen phosphate, magnesium oxide, microcrystalline cellulose, titanium dioxide and/or iron oxide are used as water-insoluble agents.

8. A drug preparation according to claim 6 wherein the water-soluble agent is selected from the group consisting of polyvinyl pyrrolidone, polyvinyl alcohol, hydroxypropyl cellulose, hydroxypropyl methyl cellulose, methyl cellulose, sodium carboxymethyl cellulose, polyoxyethylene-20-sorbitan-monooleate, sucrose, xylitol, sorbitol, mannitol, maltose, xylose, glucose, potassium chloride, sodium chloride, polyethylene glycol, propylene glycol, sodium citrate and mixtures thereof.

9. A drug preparation according to claim 1 wherein the adjuncts comprising the membrane layer include plasticizers.

10. A drug preparation according to claim 1 wherein the membrane layer contains 45–55% by weight of copolymerisate with neutral character based on poly-acrylic and methacrylic acid esters, 5–10% by weight of polyvinyl pyrrolidone, 0.5–1.5% by weight of polyoxyethylene-20-sorbitan-monooleate, 0.5–1.5% by weight of red iron oxide, 15–30% by weight of talc, 10–15% by weight of magnesium stearate and if necessary 0.01–0.1% by weight of silicone antifoam, based in each case on the membrane layer.

11. A drug preparation according to claim 1 wherein 60–90% by weight of the film coating resistant to gastric juice consists of an acid-insoluble polymer, and 10–40% by weight of the film coating consists of adjuncts.

12. A drug preparation according to claim 1 wherein the film coating resistant to gastric juice comprises a methacrylic acid polymer selected from the group consisting of methacrylic acid and ethyl acrylate copolymerisate with anionic character; acrylic and methacrylic acid ester copolymerisates with one quaternary ammonium group in relation to 20 neutral acrylic and methacrylic acid ester groups; acrylic and methacrylic acid ester copolymerisates with one quaternary ammonium group in relation to 40 neutral acrylic and methacrylic acid ester groups; and mixtures thereof.

13. A drug preparation according to claim 1 wherein the film coating resistant to gastric juice makes up 5–20% by weight, based on the final pellets, and contains 70–80% by weight, of methacrylic acid and ethyl acrylate copolymerisate with anionic character, 10–20% by weight, of diethyl phthalate, 5–15% by weight, of talc.

14. A drug preparation according to claim 1 wherein the inert pellet makes up 20–45% by weight of the final pellets, the active ingredient layer contains 20–45% by weight of diclofenac and 1–15% by weight of adjuvants, based in each case on the final pellets, the membrane layer contains 6–14% by weight of copolymerisate with neutral character based on poly-acrylic and methacrylic acid esters (solids content), 0.5–4% by weight of polyvinyl pyrrolidone, 0.05–1% by weight of polyoxyethylene-20-sorbitan-monooleate, 0.05–3% by weight of red iron oxide, 1–6% by weight of talc and 0.5–3% by weight of magnesium stearate, based in each case on the final pellets, and the film coating resistant to gastric juice contains 5–15% by weight of methacrylic acid and ethyl acrylate copolymerisate with anionic character, (solids content), and 1–8% by weight of diethyl phthalate and talc, based in each case on the final pellets.

15. A drug preparation according to claim 1 wherein the inert pellet makes up 31% by weight of the final pellets, the active ingredient layer contains 31% by weight of diclofenac, 6% by weight of polyvinyl pyrrolidone, 1% by weight of polyethylene glycol 400, 2% by weight of talc, if necessary a silicone antifoam and 3% by weight of nicotinamide, the membrane layer contains 8% by weight of copolymerisate with neutral character based on poly-acrylic and methacrylic acid esters (solids content), 0.2% by weight of polyoxyethylene-20-sorbitan-monooleate, 1.5% by weight of polyvinyl pyrrolidone, 0.15% by weight of red iron oxide, 3.5% by weight of talc, 2% by weight of magnesium stearate and if necessary a silicone antifoam, and the film coating resistant to gastric juice contains 7.5% by weight of methacrylic acid and ethyl acrylate copolymerisate with anionic character, (solids content), 1.5% by weight of diethyl phthalate and 1% by weight of talc, based in each case on the final pellets, and if necessary a silicone antifoam.

16. A drug preparation according to claim 1 wherein the inert pellet makes up 33.3% by weight of the final pellets, the active ingredient layer contains 33.3% by weight of diclofenac, 3.3% by weight of polyvinyl pyrrolidone, 0.5% by weight of polyethylene glycol 400, 0.2% by weight of magnesium stearate and if necessary a silicone antifoam, the membrane layer contains 7% by weight of copolymerisate with neutral character based on poly-acrylic and methacrylic acid esters, (solids content), 0.17% by weight of polyoxyethylene-20-sorbitan-monooleate, 1.2% by weight of polyvinyl pyrrolidone, 0.11% by weight of red iron oxide, 2.9% by weight of talc, 1.75% by weight of magnesium stearate and if necessary a silicone antifoam, and the film coating resistant to gastric juice contains 11.9% by weight of methacrylic acid and ethyl acrylate copolymerisate with anionic character, (solids content), 2.4% by weight of diethyl phthalate and 1.6% by weight of talc, based in each case on the final pellets, and if necessary a silicone antifoam.

17. A pelleted oral drug preparation containing diclofenac or one of its salts, with controlled release of the active ingredient, according to claim 1 wherein the approximate in vitro release rate is >15% of active ingredient after 1 hour, >30% after 2 hours, >50% after 3 hours, >70% after 4 hours and >80% after 5 hours.

18. A capsule, containing 75 mg of diclofenac or one of its salts in the form of pellets according to claim 1.

19. A method of controlling rheumatic diseases in warm-blooded animals by the administration of an active amount of a drug preparation according to claim 1.

20. A method according to claim 19 wherein a drug preparation comprising a pelleted oral drug preparation containing diclofenac or one of its salts, with controlled release of the active ingredient, which comprises an active ingredient layer built up on an inert pellet, an inner membrane layer containing 35–65% by weight of a water-insoluble polymer, 5–20% by weight of a pore-forming agent and 20–50% by weight of adjuncts, and an outer film coating resistant to gastric juice is administered twice a day in an amount of 50–150 mg. per administration.

21. A process for the manufacture of a drug preparation containing diclofenac or one of its salts, with controlled release of the active ingredient, according to claim 1, wherein in a first process step the active ingredient layer is formed by spraying inert pellets with a suspension containing the active ingredient, in a second process step the agents forming the membrane layer are sprayed on to the active ingredient layer, and in a third process step the suspended agents forming the film coating resistant to gastric juice are sprayed on to the membrane layer, the pellets are dried and those with the suitable grain size of >0.8 mm and <1.4 mm are then sieved out.

22. A process according to claim 21 which is carried out in a fluidized-bed spray unit preferably having a Wurster insert.

23. A process according to claim 21 which is carried out in a fluidized-bed spray unit having a rotor processor insert.

24. A process according to claim 21 wherein the suspended agents comprise water.

25. A drug preparation according to claim 2 wherein the inner membrane layer contains 45–55% by weight of a water-insoluble polymer, 6–13% by weight of a pore-forming agent and 25–46% by weight of adjuncts.

26. A drug preparation according to claim 4 wherein the binder is selected from the group consisting of polyvinyl pyrrolidone, hydroxypropyl cellulose, hydroxypropyl methyl cellulose, methyl cellulose, sodium carboxymethyl cellulose, and mixtures thereof.

27. A drug preparation according to claim 1 wherein the adjuncts comprising the inner membrane layer include at least one lubricant.

28. A drug preparation according to claim 1 wherein the adjuncts comprising the inner membrane layer include at least one release agent.

29. A drug preparation according to claim 28 wherein the release agent is selected from the group consisting of magnesium stearate, silicium dioxide, and talc, and mixtures thereof.

30. A drug preparation according to claim 1 wherein the adjuncts comprising the inner membrane layer include at least one plasticizer.

31. A drug preparation according to claim 30 wherein the plasticizer is polyethylene glycol 400.

32. A drug preparation according to claim 1 wherein the adjuncts comprising the inner membrane layer include a silicone antifoam.

33. A drug preparation according to claim 1 wherein the adjuncts comprising the inner membrane layer include an indicator.

34. A drug preparation according to claim 33 wherein the indicator is nicotinamide.

35. A drug preparation according to claim 9 wherein the plasticizer is selected from the group consisting of triacetin, diethyl phthalate, and mixtures thereof.

36. A drug preparation according to claim 11, wherein 75% by weight of the film coating resistant to gastic juice consists of an acid-insoluble polymer, and 25% by weight consists of adjuncts.

37. A drug preparation according to claim 27 wherein the lubricant is selected from the group consisting of talc, magnesium stearate, silicium dioxide, and mixtures thereof.

38. A drug preparation according to claim 12 wherein the film coating resistant to gastric juice further comprises a cellulose derivative selected from the group consisting of cellulose acetate phthalate, carboxy methyl ethyl cellulose, and mixtures thereof.

39. A drug preparation according to claim 12 wherein the film coating resistant to gastric juice further comprises a plasticizer selected from the group consisting of diethyl phthalate, triacetin, dibutyl sebacate, diethyladipate, polyethylene glycol, tributyl citrate, and mixtures thereof.

40. A drug preparation according to claim 12 wherein the film coating resistant to gastric juice further comprises a releasing agent selected from the group consisting of talc, silicium dioxide and mixtures thereof.

41. A drug preparation according to claim 12 wherein the film coating resistant to gastric juice further comprises a colored pigment selected from the group consisting of iron oxide, titanium dioxide, and mixtures thereof.

42. A drug preparation according to claim 12 wherein the film coating resistant to gastric juice further comprises a silicone antifoam.

43. A drug preparation according to claim 13 wherein the film coating resistant to gastric juice makes up 10–16% by weight, based on the final pellets, and contains 75% by weight of methacrylic acid or ethyl acrylate copolymerisate with anionic character, 15% by weight of diethyl phthalate, and 10% by weight of talc.

44. A drug preparation according to claim 1 wherein the film coating resistant to gastric juice further comprises a silicone antifoam.

45. A method according to claim 20 comprising administering 75 mg of diclofenac Na per administration.

46. A drug preparation according to claim 43 wherein the film coating resistant to gastric juice further comprises a silicone antifoam.

47. A drug preparation according to claim 1 wherein the film coating resistant to gastric juice makes up 10–16% by weight, based on the final pellets.

* * * * *